(12) United States Patent
Yu

(10) Patent No.: US 11,801,378 B2
(45) Date of Patent: Oct. 31, 2023

(54) INTERVENTIONAL VENTRICULAR ASSIST DEVICE

(71) Applicant: SHENZHEN CORE MEDICAL TECHNOLOGY CO., LTD., Shenzhen (CN)

(72) Inventor: Shunzhou Yu, Shenzhen (CN)

(73) Assignee: SHENZHEN CORE MEDICAL TECHNOLOGY CO., LTD., Shenzhen (CN)

( * ) Notice: Subject to any disclaimer, the term of this patent is extended or adjusted under 35 U.S.C. 154(b) by 174 days.

(21) Appl. No.: 17/429,951

(22) PCT Filed: Dec. 30, 2020

(86) PCT No.: PCT/CN2020/141796
§ 371 (c)(1),
(2) Date: Aug. 11, 2021

(87) PCT Pub. No.: WO2022/021798
PCT Pub. Date: Feb. 3, 2022

(65) Prior Publication Data
US 2023/0144798 A1     May 11, 2023

(30) Foreign Application Priority Data

Jul. 31, 2020   (CN) .......................... 202010758361.8

(51) Int. Cl.
*A61M 60/82*       (2021.01)
*F04D 13/06*       (2006.01)
(Continued)

(52) U.S. Cl.
CPC .............. *A61M 60/82* (2021.01); *F04D 13/06* (2013.01); *F04D 25/082* (2013.01); *F04D 29/0413* (2013.01); *F04D 29/181* (2013.01)

(58) Field of Classification Search
CPC .......... F04D 3/00; F04D 13/026; F04D 13/06; F04D 29/0413; F04D 29/0476; F04D 29/048; F04D 29/181; A61M 60/82
See application file for complete search history.

(56) References Cited

U.S. PATENT DOCUMENTS

2011/0238172 A1* 9/2011 Akdis .................. A61M 60/117
                                                               623/3.11
2015/0038770 A1   2/2015 Colella
(Continued)

FOREIGN PATENT DOCUMENTS

CN          104274873 A    1/2015
CN          110237327 A    9/2019
(Continued)

*Primary Examiner* — Kenneth J Hansen
(74) *Attorney, Agent, or Firm* — SOROKER AGMON NORDMAN PTE LTD

(57) ABSTRACT

An interventional ventricular assist device (100), including: an interventional tube (10). a motor assembly (30), a perfusion cylinder (40), and an impeller assembly (20). The interventional tube (10) has a liquid inlet (11) and a liquid outlet (12). The impeller assembly (20) includes an impeller (21), accommodated within the interventional tube (10) and rotatable to enable a liquid to flow into the interventional tube (10) via the liquid inlet (11) and out therefrom via the liquid outlet (12). The motor assembly (30) is configured to generate a rotating magnetic field to drive the impeller (21) to rotate and generate an attraction to the impeller (21). A perfusate injected from the perfusion cylinder (40) is adapted to provide a thrust to the impeller assembly (20), whereby the impeller (21) is suspendedly rotatable in the interventional tube (10) under a combined action of the thrust and the attraction.

18 Claims, 16 Drawing Sheets

(51) Int. Cl.
    *F04D 25/08*     (2006.01)
    *F04D 29/041*     (2006.01)
    *F04D 29/18*     (2006.01)

(56) References Cited

U.S. PATENT DOCUMENTS

| | | | | |
|---|---|---|---|---|
| 2015/0051436 | A1* | 2/2015 | Spanier | A61M 60/237 |
| | | | | 600/16 |
| 2016/0375187 | A1 | 12/2016 | Lee et al. | |
| 2018/0050142 | A1* | 2/2018 | Siess | A61M 60/824 |
| 2022/0288379 | A1* | 9/2022 | Kerkhoffs | A61M 60/221 |

FOREIGN PATENT DOCUMENTS

| | | | |
|---|---|---|---|
| CN | 111840683 | A | 10/2020 |
| CN | 212308654 | U | 1/2021 |

\* cited by examiner

INTERVENTIONAL VENTRICULAR ASSIST DEVICE

This application claims priority to Chinese Patent Application No. 202010758361.8, titled "interventional ventricular assist device", filed Jul. 31, 2020, the contents of which are incorporated herein by reference.

TECHNICAL FIELD

The present application relates to the technical field of medical devices, and more particularly to an interventional ventricular assist device.

BACKGROUND

The statements herein only provide background information related to the present application, and do not necessarily constitute prior art. A traditional interventional ventricular assist device adopts a mechanical bearing to achieve rotation of an impeller, which, however, has mechanical friction, and will bring potential risk of blood compatibility, and a bearing joint of the mechanical bearing is prone to thrombosis formation.

Technical Problems

It is an objective of the present application to provide an interventional ventricular assist device, which aims at solving the technical problem in the conventional interventional ventricular assist device that the risk of blood compatibility is resulted from the mechanical friction.

Technical Solutions

In order to solve the above-described technical problems, technical solutions adopted by embodiments of the present application are as follows:

In one aspect, it is provided an interventional ventricular assist device, which comprises: an interventional tube, a motor assembly, a perfusion cylinder, and an impeller assembly.

The interventional tube has a liquid inlet and a liquid outlet.

The impeller assembly comprises an impeller, the impeller is accommodated within the interventional tube, and the impeller is rotatable to enable a liquid to flow into the interventional tube via the liquid inlet and out therefrom via the liquid outlet.

The motor assembly is configured to generate a rotating magnetic field to drive the impeller to rotate and generate an attraction to the impeller.

The perfusion cylinder is configured to inject a perfusate into the interventional tube and enable the perfusate injected from the perfusion cylinder to provide a thrust to the impeller assembly, whereby the impeller is suspendedly rotatable in the interventional tube under a combined action of the thrust and the attraction.

Advantages

Advantages of the interventional ventricular assist device provide by embodiments of the present application are summarized as follows: In the interventional ventricular assist device provided by embodiments the present application, and the motor assembly is configured to generate a rotating magnetic field to drive the impeller to rotate and generate an attraction to the impeller. A perfusate injected from the perfusion cylinder provide a thrust to the impeller assembly, such that the impeller is suspendedly rotatable under a combined action of the thrust and the attraction. Compared with the mechanical bearing, the mechanical friction between the impeller and other parts is avoided, such that not only is the risk of blood contamination by abrasive particles generated from the mechanical friction avoided, but also the risk of thrombus formation at the mechanical bearing is avoided. Meanwhile, compared with the utilization of a flexible part to drive the impeller to rotate, the interventional ventricular assist device according to embodiments of the present application generates less vibration, which makes the patient feel more comfortable.

BRIEF DESCRIPTION OF THE DRAWINGS

In order to more clearly illustrate the technical solutions in the embodiments of the present application, the drawings that need to be used in the description of the embodiments or the prior art will be briefly described hereinbelow. Obviously, the accompanying drawings in the following description are only some embodiments of the present application. For those skilled in the art, other drawings can be obtained based on these drawings without creative work.

Figure 1:
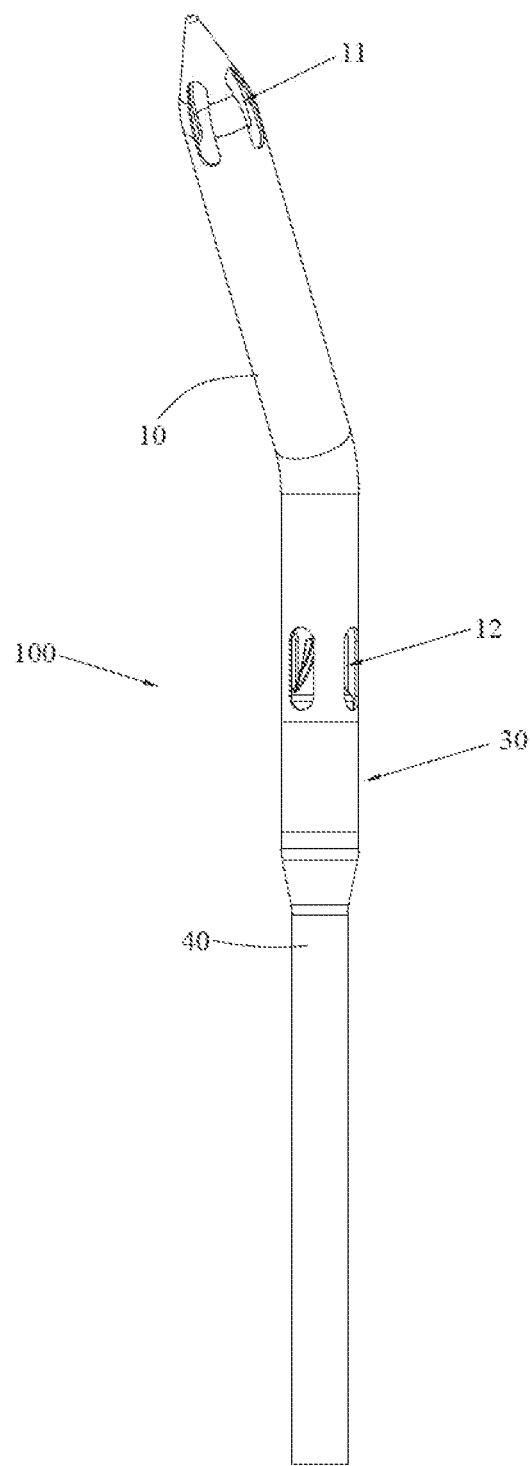
FIG. 1 is a perspective view of an interventional ventricular assist device provided by an embodiment of the present application.

In the drawings, the following reference numerals are adopted:

100: Interventional ventricular assist device; 10: Interventional tube; 11: Liquid inlet; 12: Liquid outlet; 13: First channel; 14: Straight tubular segment; 15: Bend tubular segment; 20: Impeller assembly; 21: Impeller; 211: Hub; 2111: First installation groove; 2111a: Straight hole portion; 2111b: Inclined hole portion; 2112: Second installation groove; 2113: Flow guiding hole; 2114: Blade; 2115: Cylindrical segment; 2116: Conical segment; 212: Magnetic member; 213: Seal cover; 22: Transmission shaft; 30: Motor assembly; 31: Stator; 32: Motor casing; 321: Annular groove; 322: Limiting groove; 3221: Groove opening; 3222:

Bottom wall; 323: Cylinder; 324: Hole assembly; 3241: First hole; 3242: Second hole; 325: Step; 33: Cover plate; 331: Through hole; 40: Perfusion cylinder; 41: Second channel; and 42: Cable outlet.

DETAILED DESCRIPTION OF THE EMBODIMENTS

In order to make the purposes, technical solutions, and advantages of the present application clearer and more understandable, the present application will be further described in detail hereinafter with reference to the accompanying drawings and embodiments. It should be understood that the embodiments described herein are only intended to illustrate but not to limit the present application.

It should be noted that when an element is described as "fixed" or "arranged" on/at another element, it means that the element can be directly or indirectly fixed or arranged on/at another element. When an element is described as "connected" to/with another element, it means that the element can be directly or indirectly connected to/with another element. Terms "upper", "lower", "left", "right", and the like indicating orientation or positional relationship are based on the orientation or the positional relationship shown in the drawings, and are merely for facilitating and simplifying the description of the present application, rather than indicating or implying that a device or component must have a particular orientation, or be configured or operated in a particular orientation, and thus should not be construed as limiting the application. The terms "first" and "second" are adopted for descriptive purposes only and are not to be construed as indicating or implying a relative importance or implicitly indicating the number of technical features indicated. The meaning of "a plurality of" or "multiple" is two or more unless otherwise specifically defined.

Technical solutions of the present application will be described in details in combination with the specific drawings and embodiments.

As shown in FIGS. 1-6, an embodiment of the present application provides an interventional ventricular assist device 100, and more particularly to a centrifugal magnetic suspension ventricular assist device. The interventional ventricular assist device 100 can be applied in a right ventricle as well as a left ventricle. When being applied in the left ventricle, the interventional ventricular assist device can be inserted into the left ventricle via an aorta. The interventional ventricular assist device 100 comprises: an interventional tube 10, an impeller assembly 20, a motor assembly 30, and a perfusion cylinder 40. In an embodiment as illustrated, the motor assembly 30 is connected between the interventional tube 10 and the perfusion cylinder 40. The motor assembly 30 is adapted to generate a rotating magnetic field, and the impeller assembly 20 is adapted to rotate under the rotating magnetic field generated by the motor assembly 30, so as to provide a thrust for impelling the liquid (for example, the blood) to flow.

Figure 2:
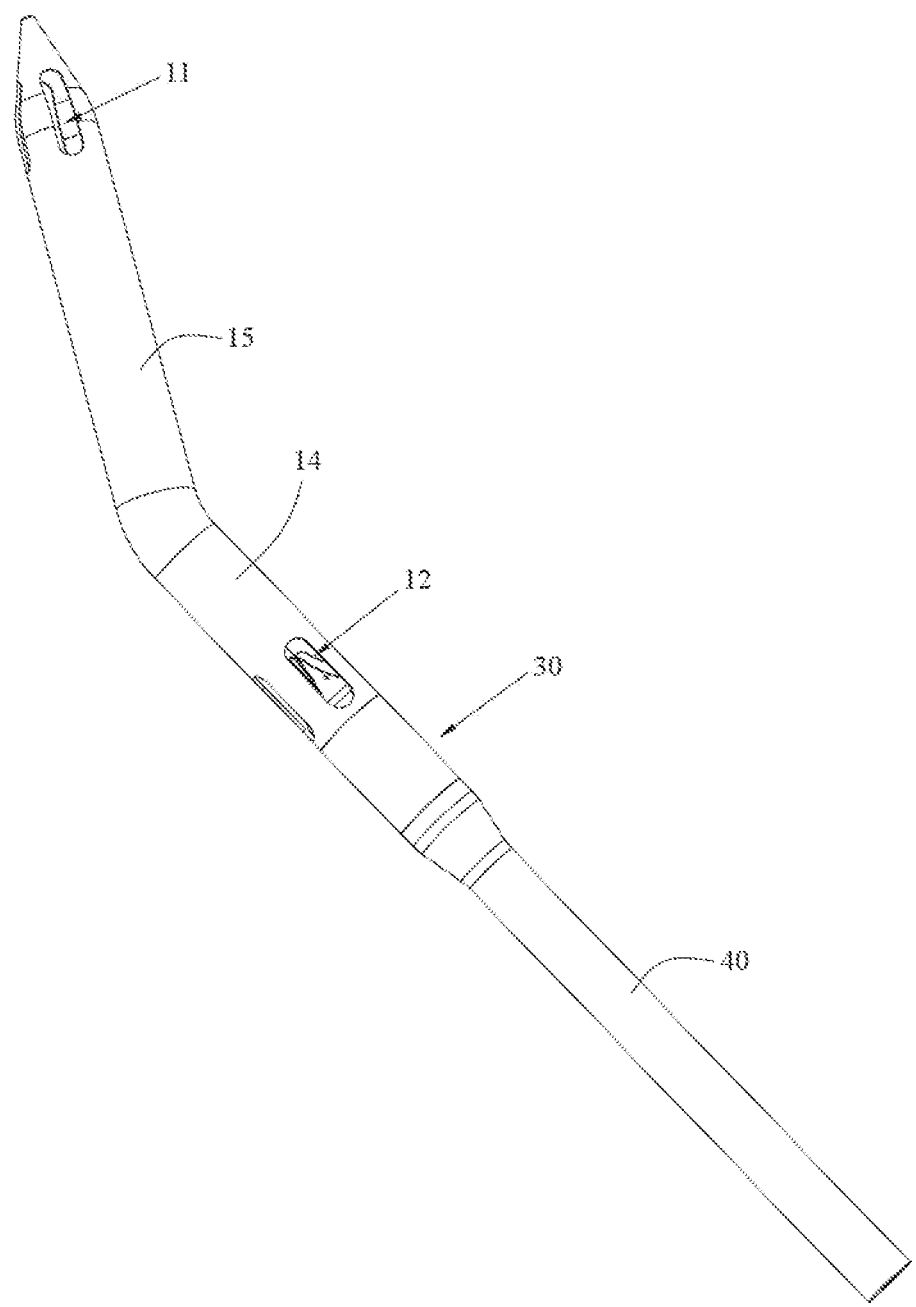
FIG. 2 is another perspective view of the interventional ventricular assist device of FIG. 1.

As shown in FIGS. 1-2, the interventional tube 10 comprises a liquid inlet 11 and a liquid outlet 12. The liquid inlet 11 is configured to allow the blood to enter the interventional tube 10, and the liquid outlet 12 is configured to allow the blood to flow out of the interventional tube 10. In the illustrated embodiment, the liquid inlet 11 and the liquid outlet 12 are arranged at two ends of the interventional tube 10, respectively. In an embodiment, the interventional tube 10 has an outer diameter fitted with an inner diameter of the aorta. The interventional tube 10 has a generally conical tip, which facilitates insertion into the blood vessel. The liquid inlet 11 is defined in the tip, and a plurality of the liquid inlets 11 are arranged at intervals around a center axis of the tip. In particular, the liquid outlet 12 is defined in a wall of the interventional tube 10 at an end thereof far away from the liquid inlet 11, that is, the liquid outlet 12 is radially arranged (herein, the direction of the rotation axis of the impeller assembly 20 is defined as the axial direction, and the direction perpendicular to the rotation axis of the impeller assembly 20 is defined as the radial direction). A plurality of the liquid outlets 12 are provided, and the plurality of the liquid outlets 12 are arranged at intervals in a circle around the central axis of the interventional tube 10. In particular, the interventional tube 10 comprises: a straight tubular segment 14, and a bend tubular segment 15 bent and extended from one end of the straight tubular segment 14, and an end of the straight tubular segment 14 far away from the bend tubular segment 15 is in fixed connection with a motor assembly 30, the liquid inlet 11 is arranged at an end of the bend tubular segment 15 far away from the straight tubular segment 14, the liquid outlet 12 is arranged at a wall of the straight tubular segment 14 at the end thereof far away from the bend tubular segment 15, the impeller 21 is rotatably accommodated in the straight tubular segment 14. The conical tip is arranged at the end of the bend tubular segment 15 far away from the straight tubular segment 14.

It should be noted that the number of the liquid outlet 12 and the number of the liquid inlet 11 are not restricted to a plural, and can also be only one, respectively. The number of the liquid outlet 12 and the number of the liquid inlet 11 can be provided according to practical needs.

The impeller assembly 20 comprises an impeller 21. The impeller 21 is accommodated in the interventional tube 10 and rotatable to enable the liquid to enter the interventional tube 10 via the liquid inlet 11 and to flow out via the liquid outlet 12. That is, a rotation axis of the impeller assembly 20 is the rotation axis of the impeller 21. In particular, the impeller 21 is arranged approximate one end of the liquid outlet 12 of the interventional tube 10. When the interventional ventricular assist device 100 is applied in the left ventricle, the blood in the left ventricle enters the interventional tube 10 via the liquid inlet 11, and then flows out of the interventional tube 10 via the liquid outlet 12 and into the aorta.

Figure 6:
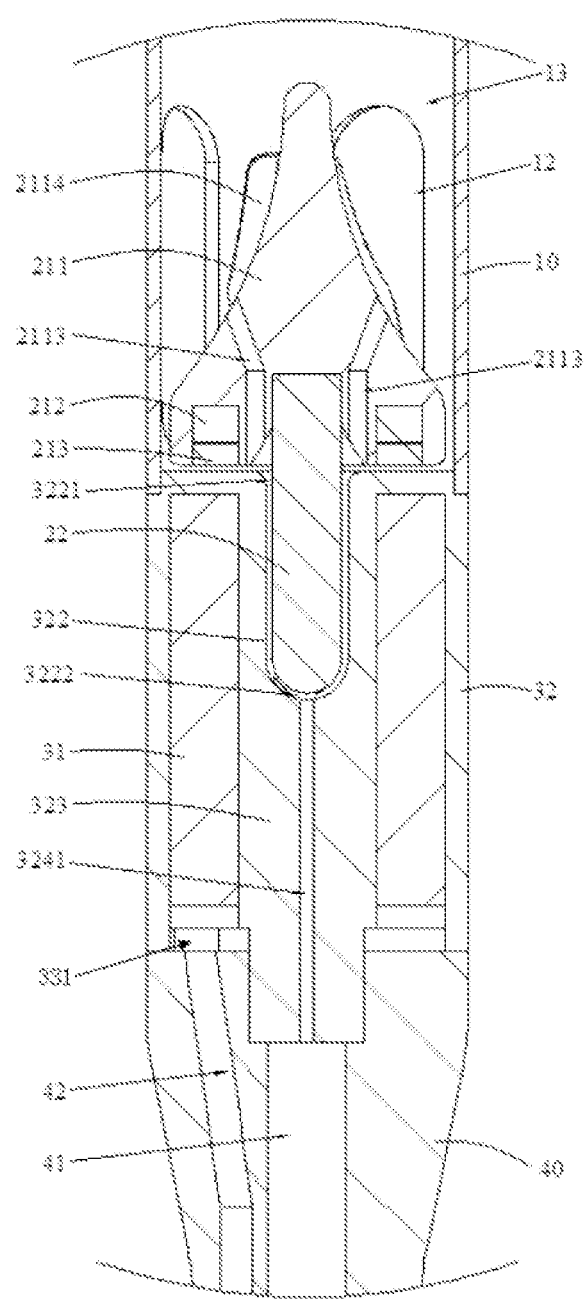
FIG. 6 is an enlarged view of a middle region of the interventional ventricular assist device of FIG. 4.

Specifically in the illustrated embodiment, as shown in FIG. 6, the impeller 21 comprises: a hub 211 and the magnetic members 212 arranged in the hub 211. The magnetic member 212 is in a ring shape, and further, the magnetic member 212 is a Halbach array magnetic ring.

The motor assembly 30 is configured to generate a rotating magnetic field to drive the impeller 21 to rotate. In particular, the motor assembly 30 is arranged at the end of the interventional tube 10 provided with the liquid outlet 12. The impeller 21 rotates under the cooperation of the magnetic member 212 and the motor assembly 30. At certain rotational speeds, a radial suspension of the impeller 21 can also be achieved under the cooperation of the magnetic member 212 and the motor assembly 30. In the present application, a state where the impeller 21 is not in contact with the sidewall of the interventional tube 10 nor the motor assembly 30 is referred to as the suspension of the impeller 21.

An attraction between the motor assembly 30 and the impeller 21 is adapted to be generated, so that the impeller 21 has a tendency to move toward the direction of the motor assembly 30. In order to achieve a balance in the axial direction, in the present application, the perfusion liquid is utilized to apply a hydraulic thrust to the impeller 21. The hydraulic thrust includes at least a force urging the impeller 21 to move in a direction far away from the motor assembly 30, whereby the suspension of the impeller 21 in the axial direction is realized. A perfusion cylinder 40 can be used to inject the perfusate into the interventional tube 10, and the perfusate injected from the perfusion cylinder 40 is configured to provide a thrust to the impeller assembly 20 so that the impeller 21 is suspendedly rotatable in the interventional tube 10 under a combined action of the motor assembly 30 and the perfusion liquid. That is, the impeller 21 is suspendedly rotatable under a combination of the action between the motor assembly 30 and the impeller 21 and the action of the perfusate to the impeller assembly 20. In other words, the thrust is adapted to offset at least the attraction between the motor assembly 30 and the magnetic member 212 of the impeller 21, so that the impeller 21 is suspended in the axial direction. The suspension rotation of the impeller 21 results in that almost no mechanical friction exists between the impeller 21 and the interventional tube 10.

In the interventional ventricular assist device 100 provided by the present application, a rotating magnetic field is generated by the motor assembly 30 to drive the impeller 21 to rotate, and a thrust is applied by the perfusate to the impeller 21, so that the impeller 21 is suspended rotatable under a combination of the action between the motor assembly 30 and the impeller 21 and the action of the perfusate to the impeller assembly 20. Compared with the mechanical bearing, the mechanical friction between the impeller 21 and other parts is avoided in the present application, such that not only is the risk of blood contamination by abrasive particles generated from the mechanical friction avoided, but also the risk of thrombus formation at the mechanical bearing is avoided. Meanwhile, compared with the utilization of a flexible part to drive the impeller 21 to rotate, the interventional ventricular assist device 100 according to embodiments of the present application generates less vibration, which makes the patient feel more comfortable.

In a specific embodiment, the perfusate is a glucose containing heparin or a physiological saline containing heparin. It can be understood that, in other embodiments of the present application, the perfusate may also be the common glucose or physiological saline. The perfusate can not only provide a thrust to the impeller 21, but also wash the impeller 21 by the heparin contained therein, whereby the blood clotting is avoided and the thrombus formation is reduced.

In a specific embodiment, as shown in FIG. 6, the motor assembly 30 defines therein a limiting groove 322 and a hole assembly 324. The limiting groove 322 is in communication with the interventional tube 10, the hole assembly 324 is in communication with the limiting groove 322, and the perfusion cylinder 40 is in communication with the hole assembly 324, such that the perfusate injected via the perfusion cylinder 40 can sequentially pass through hole assembly 324 and the limiting groove 322 and then flow into the interventional tube 10. With such a configuration, the perfusate also functions in cooling down the motor assembly 30.

In a specific illustrated embodiment, the limiting groove 322 comprises: a groove opening 3221, and a bottom wall 3222 opposite to the groove opening 3221; and the groove opening 3221 is in communication with the interventional tube 10. Specifically, the limiting groove 322 further comprises a sidewall in connection with the bottom wall 3222. The sidewall has a cylindrical surface and extends along an axial direction of the impeller 21. In such condition, the bottom wall 3222 and the sidewall of the limiting groove 322 are both groove walls of the limiting groove 322.

The impeller assembly 20 further comprises a transmission shaft 22. One end of the transmission shaft 22 is in fixed connection with the impeller 21, and the other end of the transmission shaft 22 protrudes into the limiting groove 322. The transmission shaft 22 is rotatable along the impeller 21, and the other end of the transmission shaft 22 far away from the impeller 21 is suspendable in the limiting groove 322. A rotation axis of the transmission shaft 22 coincides with a rotation axis of the impeller 21. The hole assembly 324 faces the other end of the transmission shaft 22 far away from the impeller 21, and the perfusate injected into the limiting groove 322 via the hole assembly 324 is adapted to provide a thrust onto the transmission shaft 22, such that the transmission shaft 22 and the impeller 21 are suspendedly rotatable under a combined action of the motor assembly 30 and the perfusate. In such condition, during operation, the perfusate injected into the limiting groove 322 provides a thrust to the transmission shaft 22, and the transmission shaft 22 in turn transmits the thrust to the impeller 21. Specifically, the transmission shaft 22 passes through the groove opening 3221 and protrudes toward the bottom wall 3222. In the illustrated embodiment, the transmission shaft 22 is cylindrical. The end of the transmission shaft 22 far away from the impeller 21 has an end surface in a shape of a convex hemisphere. The transmission shaft 22 is arranged at the rotation axis of the impeller 21, and an extension direction of the transmission shaft 22 is consistent with the rotation axis of the impeller 21.

Figure 8:
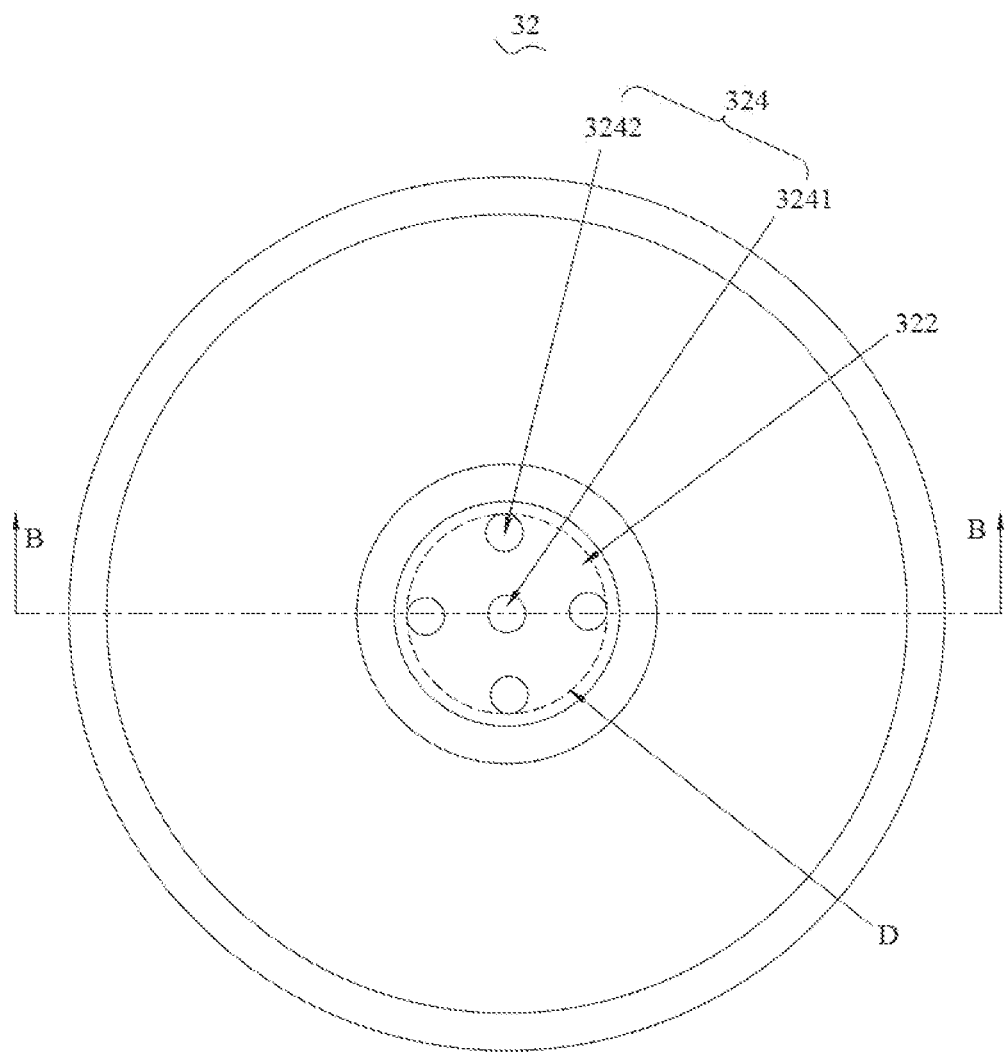
FIG. 8 is a bottom view of the motor casing of FIG. 7.
Figure 11:
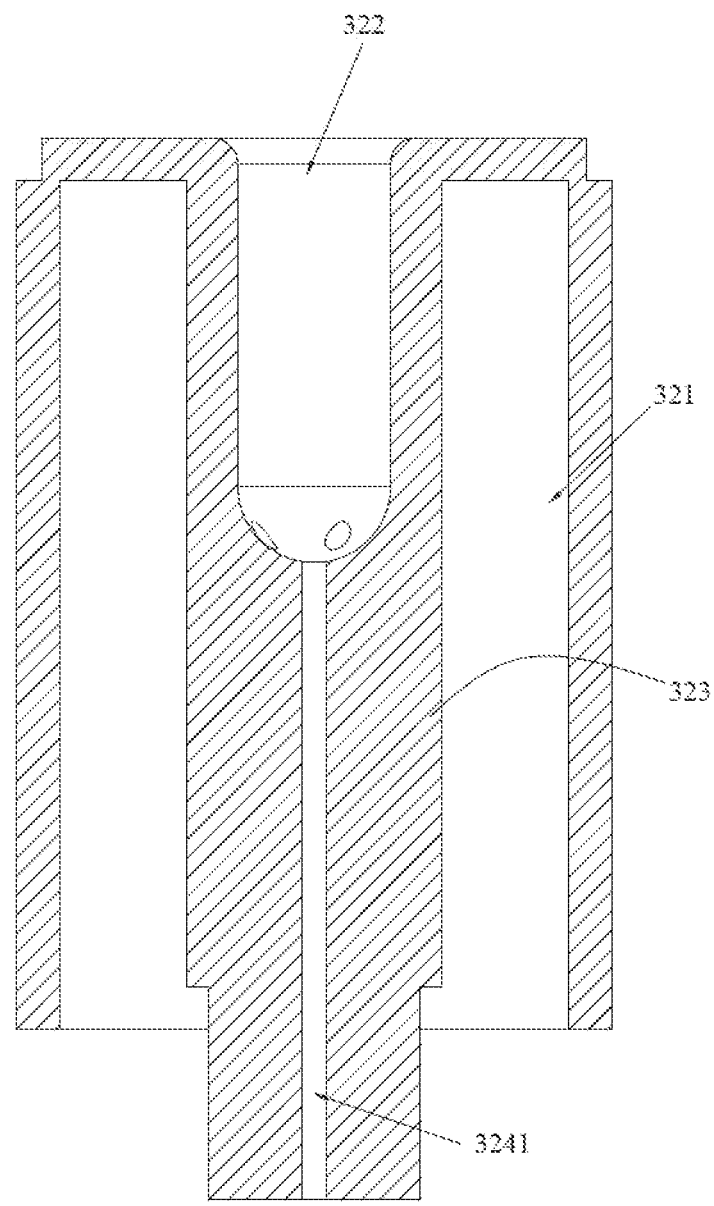
FIG. 11 is a cross section view taken from line CC of the motor casing of FIG. 10.

In a specific embodiment, as shown in FIGS. 6, 8, and 11, the hole assembly 324 includes a first hole 3241, and the first hole 3241 is in communication with the limiting groove 322 and the perfusion cylinder 40. In one of the embodiments, one opening of the first hole 3241 is defined in the bottom wall 3222, and the other opening thereof is in communication with the perfusion cylinder 40. The first hole 3241 is aligned with a center of the end surface of the end of the transmission shaft 22 away from the impeller 21. In this way, the perfusate injected from the first hole 3241 will directly act on the end surface of the end of the transmission shaft 22 far away from the impeller 21, applying a thrust to the transmission shaft 22 in the axial direction, and the thrust counteracts with the attraction of the motor assembly 30 applied to the magnetic member 212, whereby the transmission shaft 22 is balanced in the axial direction. Specifically, the central axis of the first hole 3241 coincides with the rotation axis of the transmission shaft 22. The central axis of the first hole 3241 coincides with the central axis of the limiting groove 322. It can be understood that, in other embodiments of the present application, an aperture of the first hole 3241 is the same as an aperture of the limiting groove 322, that is, the limiting groove 322 passes through the motor assembly 30 along the axial direction of the impeller 21, which is not exclusively limited herein.

Further, as shown in FIGS. 8 to 11, the hole assembly 324 further comprises a plurality of second holes 3242. The plurality of second holes 3242 are all in communication with the perfusion cylinder 40 and the limiting groove 322, the first hole 3241 is aligned with the center of the end surface of the end of the transmission shaft 22 far away from the impeller 21. The plurality of second holes 3242 are arranged at equal intervals in a circle around the first hole 3241, and the plurality of second holes 3242 face the end surface of the end of the transmission shaft 22 far away from the impeller 21. Since the end surface of the end of the transmission shaft 22 far away from the impeller 21 is in a shape of the convex hemisphere, by adopting the plurality of second holes 3242 in the above arrangement, the thrust force applied by the perfusate injected via the plurality of second holes 3242 to the transmission shaft 22 have at least a radial component or alternatively, all the thrust force is a completely radial force. In addition, as the plurality of second holes 3242 are evenly distributed in the circumferential direction, the radial thrust force exerted by the perfusate injected via the plurality of second holes 3242 onto the transmission shaft 22 can be balanced with each other, so as to further ensure the suspension balance of the transmission shaft 22 in the radial direction, and prevent the transmission shaft 22 from mechanical collision and interference with the groove wall of the limiting groove 322. In one of the embodiments, the axial directions of the plurality of second holes 3242 are parallel to the axial direction of the first hole 3241, and the plurality of second holes 3242 are arranged at equal intervals around the central axis of the first hole 3241. It should be understood that the axial directions of the plurality of second holes 3242 and the axial direction of the first hole 3241 may not be in parallel.

In a specific embodiment, as shown in FIG. 6, the bottom wall 3222 of the limiting groove 322 is in a shape of a concave hemisphere, and the first hole 3241 is arranged at a center of the bottom wall 3222. In one of the embodiments, a curvature of the bottom wall 3222 of the limiting groove 322 is consistent with a curvature of the end surface of the end of the transmission shaft 22 far away from the impeller 21. It can be understood that the curvature of the bottom wall 3222 of the limiting groove 322 may also be inconsistent with the curvature of the end surface of the end of the transmission shaft 22 far away from the impeller 21.

Figure 9:
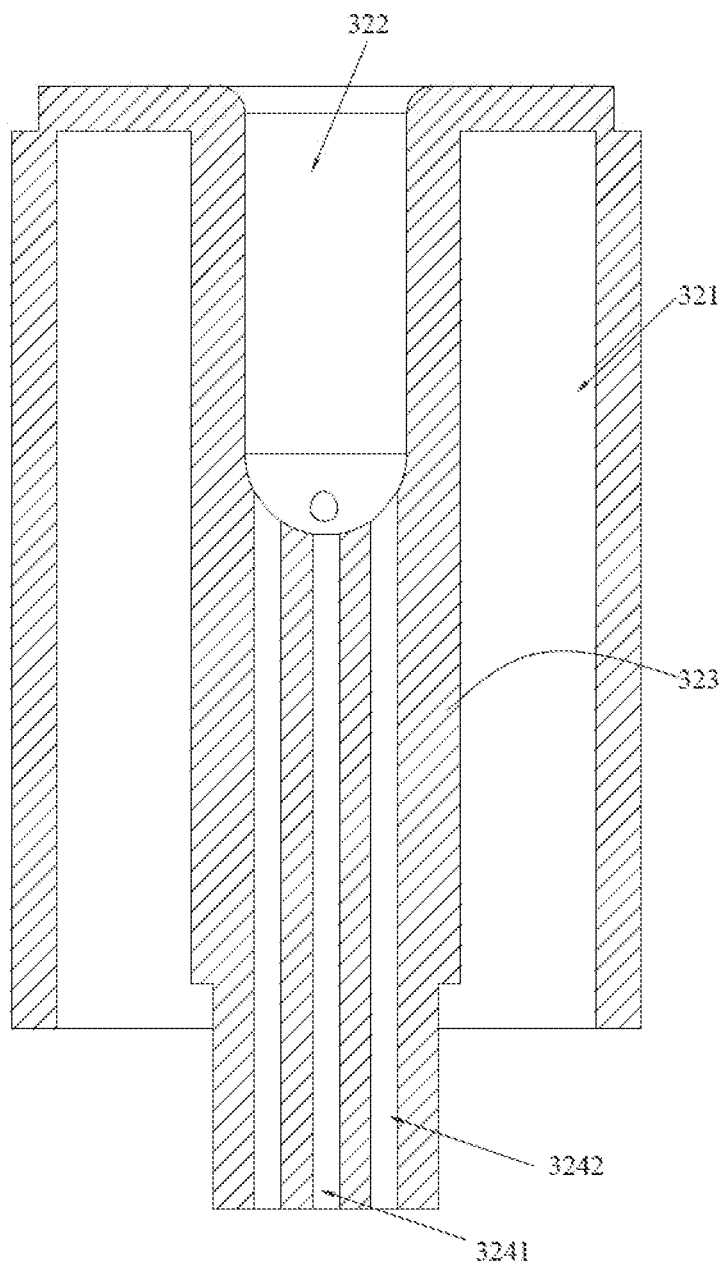
FIG. 9 is a cross section view taken from line BB of the motor casing of FIG. 8.
Figure 10:
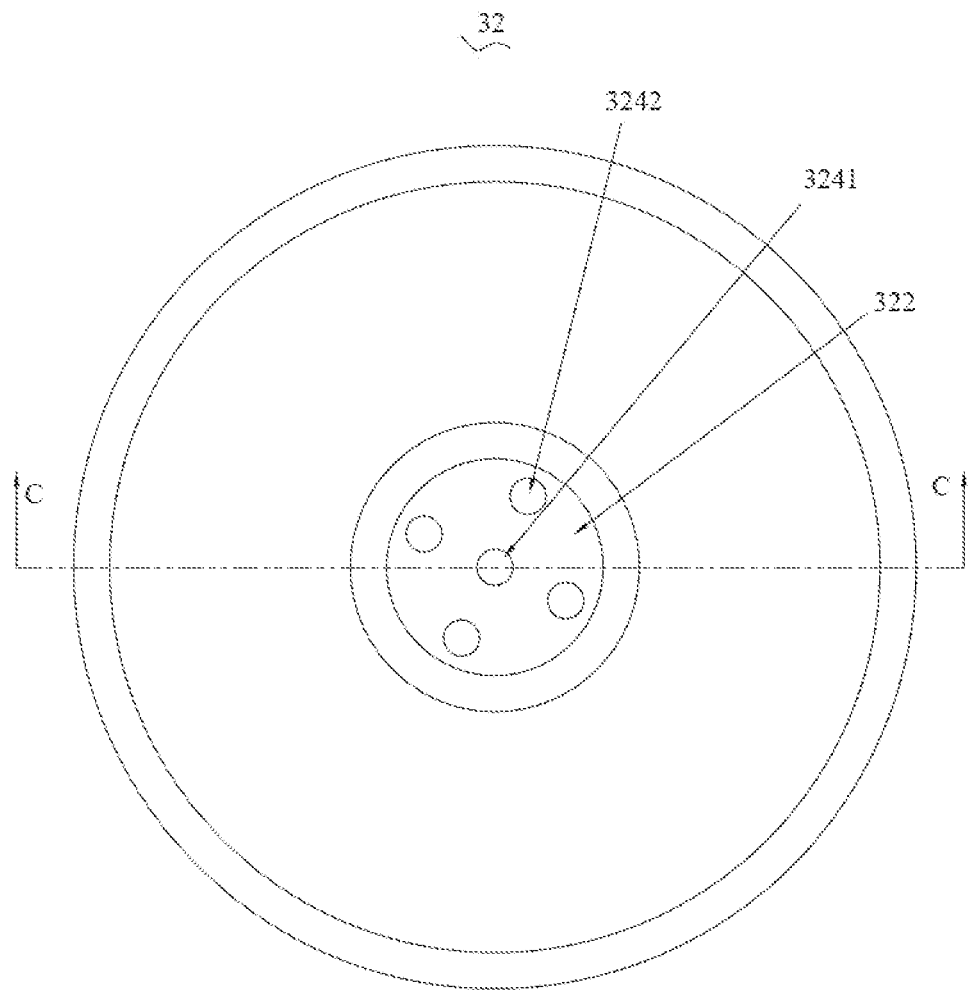
FIG. 10 is a perspective view of the motor casing of FIG. 8 from another angle.

As shown in FIGS. 9-11, in a specific illustrated embodiment, the number of the second holes 3242 is four, and the four second holes 3242 are arranged at equal intervals around the central axis of the first hole 3241, and the four second holes 3242 are defined in the bottom wall of the limiting groove 322. It can be understood that, in other embodiments of the present application, according to practical design requirements, the number of the second holes 3242 may also be three, five, or more than five, which is not exclusively limited herein.

It should be noted that the form of the hole assembly 324 is not limited to the above form. In other embodiments, the hole assembly 324 comprises a plurality of first holes 3241, and the plurality of first holes 3241 all face the end surface of the end of the transmission shaft 22 far away from the impeller 21, and the plurality of first holes 3241 are arranged at intervals around the rotation axis of the transmission shaft 22. In such condition, if the hole assembly 324 further has a plurality of second holes 3242, the plurality of second holes 3242 are arranged around the rotation axis of the transmission shaft 22 and along an outer periphery of the plurality of first holes 3241.

Figure 3:
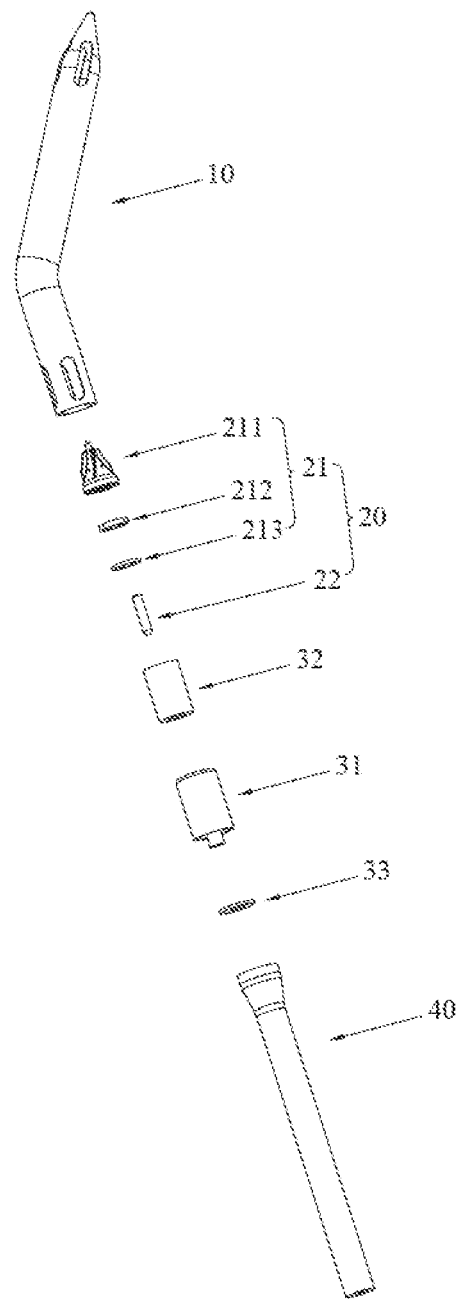
FIG. 3 is an exploded view of the interventional ventricular assist device of FIG. 2.
Figure 4:
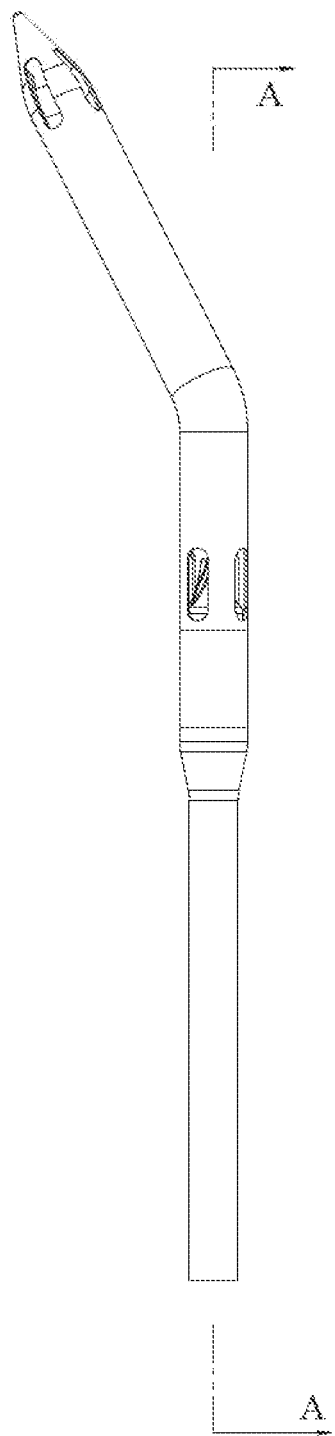
FIG. 4 is a lateral side view of the interventional ventricular assist device of FIG. 1.
Figure 5:
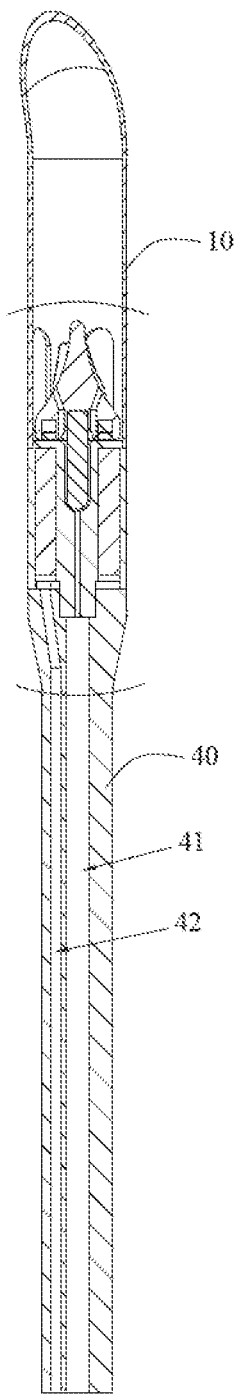
FIG. 5 is a cross section view taken from line AA of the interventional ventricular assist device of FIG. 4.

In a specific embodiment, as shown in FIGS. 1-3, the motor assembly 30 comprises a motor casing 32 and a stator 31. The motor casing 32 is in sealed connection with both the interventional tube 10 and the perfusion cylinder 40. The motor casing 32 is arranged at an end of the interventional tube 10 approximate the liquid outlet 12, and the perfusion cylinder 40 is arranged at an end of the motor casing 32 far away from the interventional tube 10. As shown in FIGS. 3 and 6, the interventional tube 10 defines therein a first channel 13, the first channel 13 is in communication with the liquid inlet 11 and the liquid outlet 12, respectively, and the impeller 21 is accommodated in the first channel 13. The stator 31 is installed and sealed within the motor casing 32. The limiting groove 322, the first hole 3241, and the second holes 3242 are all defined in the motor casing 32. The perfusion cylinder 40 defines therein a second channel 41 which is in communication with the first hole 3241 and the second holes 3242, respectively. By defining the limiting groove 322, the first hole 3241, and the second holes 3242 in the motor casing 32, the perfusate can also functions in cooling the motor assembly 30, and therefore the service life of the motor assembly 30 is increased. It can be understood that, in other embodiments of the present application, if conditions permit, the interventional tube 10, the motor casing 32, and the perfusion cylinder 40 may also be integrally formed, which is not exclusively limited herein.

As shown in FIG. 6, the stator 31 and the impeller 21 are spaced apart from each other in the axial direction, so that the impeller 21 has a larger torque, so that the impeller 21 can rotate at a lower rotational speed, thereby reducing the shear stress of the impeller 21 imposed on the blood, lowering the damage of the blood caused by the impeller 21, and reducing the hemolysis. In addition, compared to the conventional arrangement of the stator 31 surrounding the impeller 21, the impeller 21 of the present application can have a larger size, which is more convenient to manufacture, and is conducive to reduction of the manufacturing cost.

In a specific embodiment, as shown in FIGS. 3, 9 and 11, the motor casing 32 defines therein an annular groove 321, the annular groove 321 is arranged around the limiting groove 322, and the annular groove 321 is spaced apart from the limiting groove 322. In particular, the central axis of the limiting groove 322 coincides with the central axis of the motor casing 32, and the annular groove 321 and the limiting groove 322 are coaxially arranged. An opening of the annular groove 321 faces the perfusion cylinder 40, and the opening of the limiting groove 322 faces the interventional tube 10, that is, the opening of the annular groove 321 and the opening of the limiting groove 322 face different ends of the motor casing 32 in the axial direction, respectively, and the annular groove 321 and the limiting groove 322 are not in communication with each other. The stator 31 is also in an annular shape, and the stator 31 is accommodated in the annular groove 321. The opening of the annular groove 321 is covered by a cover plate 33, the cover plate 33 has an annular shape, and the cover plate 33 is provided at the annular groove 321, so that the stator 31 is mounted in the motor casing 32 in a sealed manner.

Figure 7:
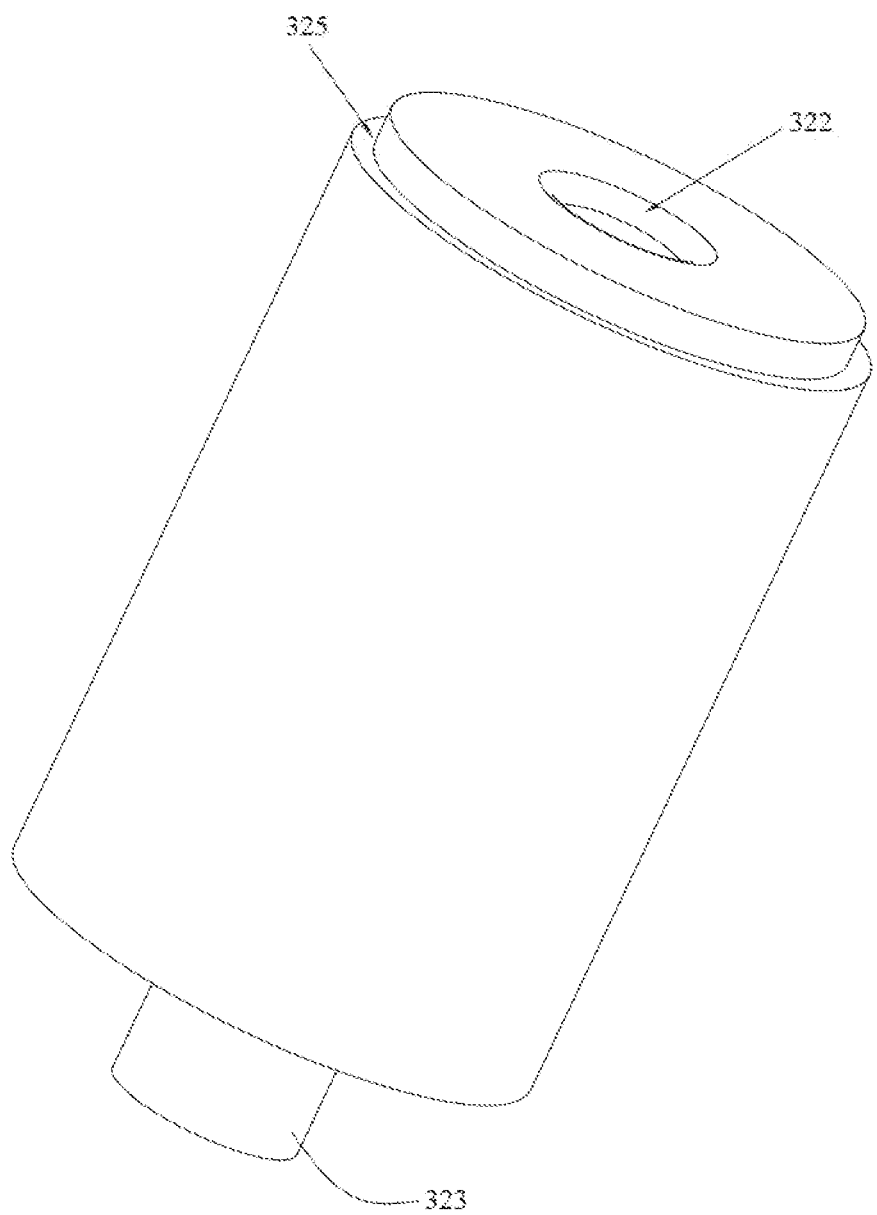
FIG. 7 is a perspective view of a motor casing of FIG. 1.

As shown in FIGS. 6-7, the motor casing 32 has a cylindrical shape as a whole. An outer wall of the motor casing 32 is flush with an outer wall of the interventional tube 10 at a junction of the motor casing 32 and the interventional tube 10, and the outer wall of the motor casing 32 is flush with an outer wall of the perfusion cylinder 40 at a junction of the motor casing 32 and the perfusion cylinder 40. Two ends of the motor casing 32 form a plug fit with the interventional tube 10 and the perfusion cylinder 40, respectively. In particular, a step 325 is formed at a periphery of one end of the motor casing 32, and the end of the interventional tube 10 far away from the liquid inlet 11 is sleeved at the step 325 of the motor casing 32 and formed a sealed connection by pasting, welding, and hot pressing, etc.

In a specific embodiment, as shown in FIG. 6, a cylinder 323 extends along a central axis of the annular groove 321, the cylinder 323 and the annular groove 321 are arranged concentrically. An end of the cylinder 323 protrudes outside of the annular groove 321, and the end of the cylinder 323 protruding from the annular groove 321 is received in the perfusion cylinder 40. The limiting groove 322, the first hole 3241, and the second holes 3242 are all formed in the cylinder 323. Specifically, the limiting groove 322 axially extends inward from one end of the cylinder 323 facing the interventional tube 10, and the first hole 3241 and the second holes 3242 axially extend inward from the other end of the cylinder 323 to the bottom wall of the limiting groove 322. The second channel 41 extends axially along the perfusion cylinder 40, the central axis of the second channel 41 coincides with the central axis of the first hole 3241, and an aperture of the second channel 41 is greater than a diameter of an outer contour circle D formed by all the second holes 3242. It should be noted herein that the outer contour circle D formed by all the second holes 3242 refers to the circle where the points of the various second holes 3242 farthest from the central axis of the first hole 3241 are arranged. Specifically, the outer contour circle D of all the second holes 3242 is indicated by a dotted circle in FIG. 8. When the aperture of the second channel 41 is greater than the diameter of the outer contour circle D of all the second holes 3242, the perfusate injected from the second channel 41 can be injected into the first hole 3241 and all the second holes 3242, such that the impeller is maintained balanced in the axial and radial direction.

As shown in FIG. 6, the perfusion cylinder 40 further defines therein a cable outlet 42, and the cable owlet 42 is spacedly arranged apart from the second channel 41. The cover plate 33 defines therein a through hole 331 with a position thereof corresponding to the cable outlet 42. A control line of the stator 31 sequentially passes through the through hole 331 and the cable outlet 42 and forms a communication connection with an external controller.

Figure 12:
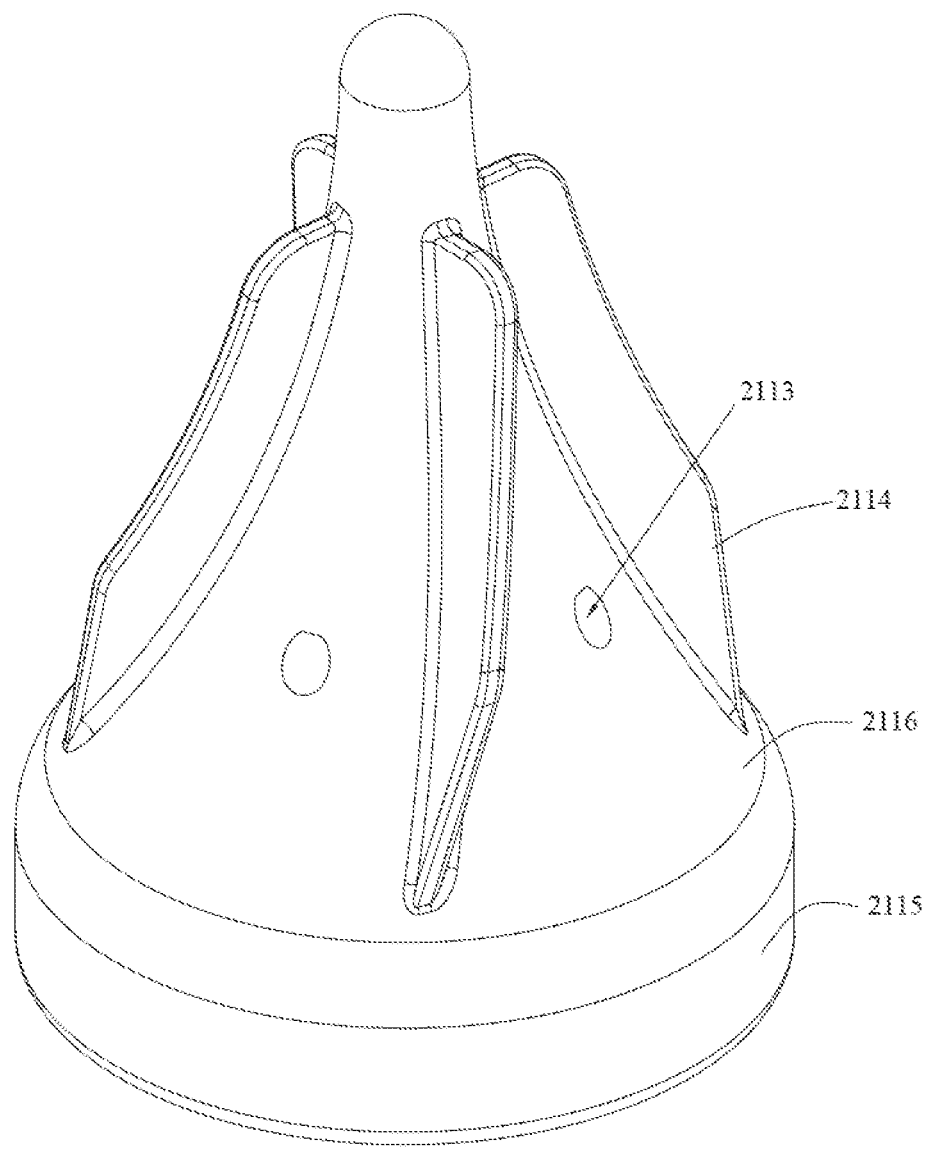
FIG. 12 is a perspective view of an impeller of FIG. 6.

As shown in FIG. 12, the impeller 21 comprises a cylindrical segment 2115 and a conical segment 2116. The cylindrical segment 2115 and the conical segment 2116 are integrally connected along the axial direction of the impeller 21. The cylindrical segment 2115 is arranged approximate the motor casing 32. The conical segment 2116 is arranged far away from the motor casing 32, and the magnetic member 212 is installed within the cylindrical segment 2115. One end of the transmission shaft 22 is installed at a center of the cylindrical segment 2115. Four blades 2114 are distributed on an outer circumference of the conical segment 2116, and each of the blades 2114 is spirally distributed on an outer wall of the conical segment 2116.

Figure 13:
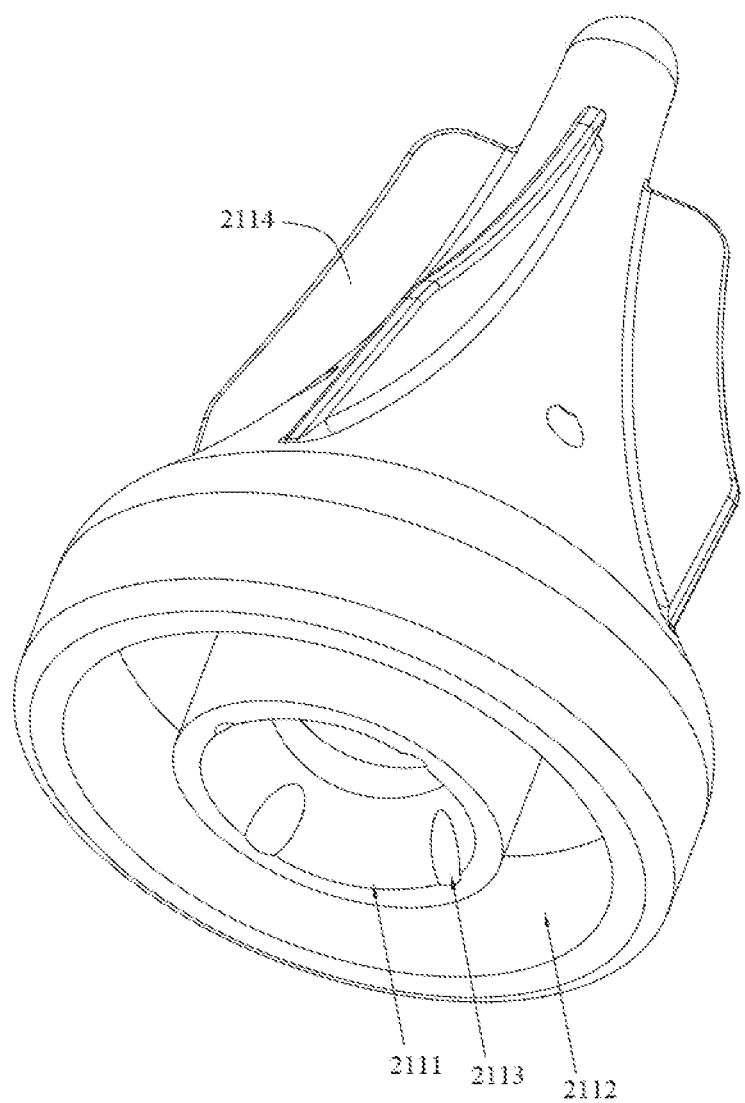
FIG. 13 is a perspective view of the impeller of FIG. 12 from another angle.
Figure 14:
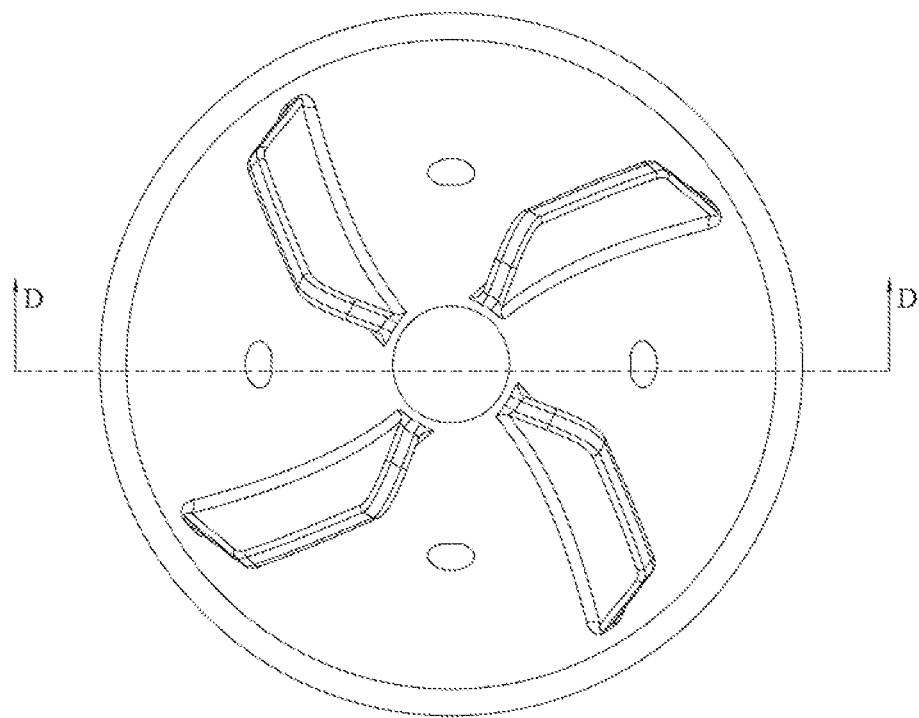
FIG. 14 is a bottom view of the impeller of FIG. 13.
Figure 15:
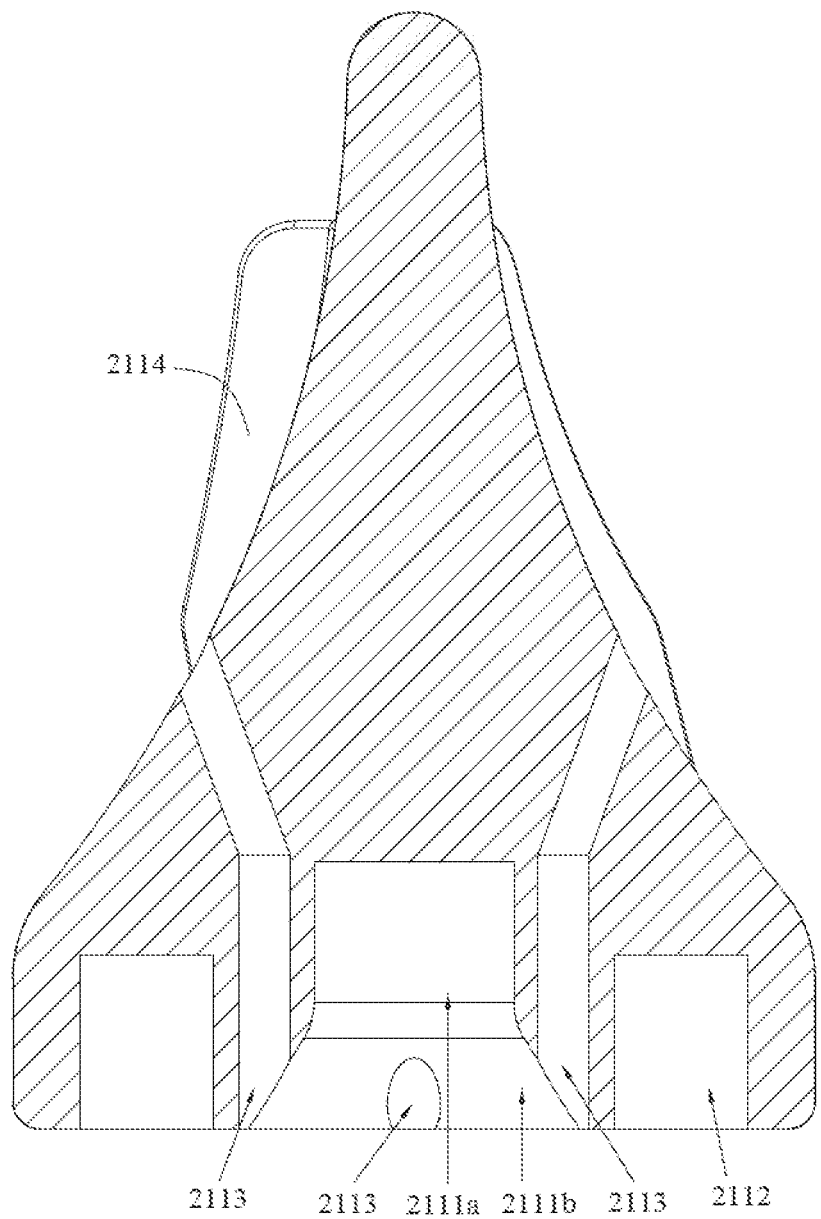
FIG. 15 is a cross section view taken from line DD of the impeller of FIG. 14.

In a specific embodiment, as shown in FIGS. 13-15, the impeller 21 defines therein a first installation groove 2111 and a second installation groove 2112. In particular, the first installation groove 2111 and the second installation groove 2112 are formed in the hub 211. Both openings of the first installation groove 2111 and the second installation groove 2112 face the motor casing 32. The first installation groove 2111 is circular and arranged in the center of the impeller 21, the second installation groove 2112 is circular and surrounds the first installation groove 2111, the second installation groove 2112 and the first installation groove 2111 are arranged concentrically, that is, a center line of the second installation groove 2112, and a center line of the first installation groove 2111, and a center line of the entire impeller 21 coincide. An end of the transmission shaft 22 away from the limiting groove 322 is accommodated in the first installation groove 2111, and the magnetic member 212 is accommodated in the second installation groove 2112, so that the magnetic member 212, the transmission shaft 22, and the impeller after installation 21 are arranged concentrically. When the stator 31 applies a rotating magnetic field to the magnetic member 212, the magnetic member 212 drives the transmission shaft 22 and the impeller 21 to rotate, and the magnetic member 212, the transmission shaft 22 and the impeller 21 coaxially rotate.

As shown in FIG. 6, the magnetic member 212 is in an annular shape and installed in the second installation groove 2112. The second installation groove 2112 is also covered with a seal cover 213, and the magnetic member 212 is sealed by the seal cover 213 and fixed In the second installation groove 2112, therefore, the magnetic member 212 is prevented from being contaminated by blood or the perfusate, which would otherwise damaging the efficacy.

As shown in FIG. 6, one end of the transmission shaft 22 is inserted into the first installation groove 2111, and the transmission shaft 22 can be fixed in the first installation groove 2111 by interference fit, welding, pasting, or fasteners.

In a specific embodiment, as shown in FIG. 6 and FIGS. 12-15, the impeller 21 defines therein a flow guiding hole 2113. The flow guiding hole 2113 has two openings. One opening of the flow guiding hole 2113 faces the liquid outlet 12, and the other opening faces the limiting groove 322. In some illustrated embodiments, the flow guiding hole 2113 is defined in the hub 211. Based on the arrangement of the flow guiding hole 2113, the perfusate injected into the limiting groove 322 from the second channel 41 can enter the interventional tube 10 through the flow guiding hole 2113 and flow out via the liquid outlet 12; meanwhile, the blood flowing from a first gap between the interventional tube 10 and the impeller 21 to a second gap between the impeller 21 and the motor casing 32 can flow back to the liquid outlet 12 through the flow guiding hole 2113 to form a secondary flow field, so as to flush the blood and reduce the blood retention. And along the radial direction of the impeller 21, the respective flow guiding holes 2113 are arranged between the first installation groove 2111 and the second installation groove 2112.

Further, a plurality of the flow guiding holes 2113 are defined in the impeller 21, the plurality of the flow guiding holes 2113 are arranged at equal intervals around the rotation axis of the impeller 21. Each of the plurality of the flow guiding holes 2113 has one opening facing one of the liquid outlets, and the other opening facing the limiting groove 322.

In an illustrated embodiment, the number of the flow guiding holes 2113 are four, and the four flow guiding holes 2113 are specifically formed in the hub 211. It should be noted that the flow guiding hole 2113 is not limited to four, the flow guiding hole 2113 can also be one, two, three, or more than four, and the number of the flow guiding hole 2113 can be determined according to practical needs.

Further, as shown in FIGS. 6 and 15, the first installation groove 2111 comprises: a straight hole portion 2111a, and an inclined hole portion 2111b in communication with the straight hole portion 2111a. An aperture of the inclined hole portion 2111b gradually increases in a direction far away from the straight hole portion 2111a. The inclined hole portion 2111b faces the limiting groove 322, and an opening of the flow guiding hole 2113 far away from the liquid outlet 12 is arranged at a sidewall of the inclined hole portion 2111b. The end of the transmission shaft 22 away from the limiting groove 322 is accommodated in the inclined hole portion 2111b and the straight hole portion 2111a, and is in fixed connection with a sidewall of the straight hole portion 2111a. In this way, after the transmission shaft 22 is installed in the first installation groove 2111, a third gap is provided between the transmission shaft 22 and an inner wall of the inclined hole portion 2111b, and the perfusate flowing out of the limiting groove 322 can directly flow into the flow guiding hole 2113 via the third gap. That is, the inclined inner wall of the inclined hole portion 2111b functions in flow guiding, which quickly guides the perfusate or blood into the flow guiding hole 2113 to form a secondary flow field.

Figure 16:
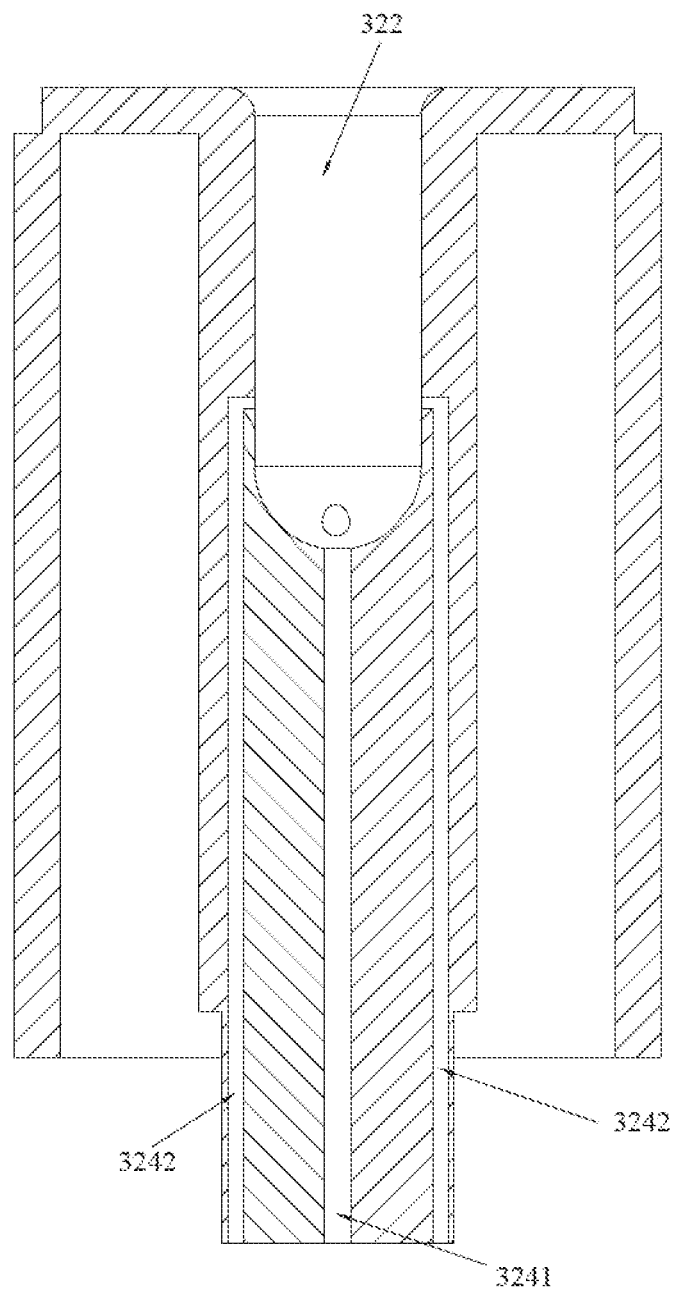
FIG. 16 is a structural view of a motor casing provided by another illustration of the present application.

In another embodiment of the present application, the hole assembly 324 and the limiting groove 322 may be connected in other ways, as shown in FIG. 16, the groove wall of the limiting groove 322 is a cylindrical surface, and the hole assembly 324 comprises a first hole 3241 and a plurality of second holes 3242, the first hole 3241 and the plurality of second holes 3242 are all in communication with the perfusion cylinder 40 and the limiting groove 322, the first hole 3241 faces an end surface of one end of the transmission shaft 22 far away from the impeller 21, and the plurality of the second holes 3242 are evenly arranged at intervals in a circle around a center line of the first hole 3241. Specifically, the plurality of second holes 3242 are arranged on the sidewall of the limiting groove 322, and the plurality of second holes 3242 face a peripheral side of the transmission shaft 22. In this way, by the arrangement of the plurality of second holes 3242, the perfusate can be introduced into the limiting groove 322 and acts on the peripheral side of the transmission shaft 22 respectively, so as to realize the radial balance of the transmission shaft 22.

The above is only the preferred embodiments of the present application, and is not intended to limit the application. For those skilled in the art, the application may have various alterations and changes. Any modifications, equivalent substitutions, and improvements made within the spirit and principles of the present application are included in the protection scope of the present application.

What is claimed is:

1. An interventional ventricular assist device, comprising: an interventional tube, a motor assembly, a perfusion cylinder, and an impeller assembly;
   wherein
   the interventional tube has a liquid inlet and a liquid outlet;
   the impeller assembly comprises an impeller, the impeller is accommodated within the interventional tube, and the impeller is rotatable to enable a liquid to flow into the interventional tube via the liquid inlet and out therefrom via the liquid outlet;
   the motor assembly is configured to generate a rotating magnetic field to drive the impeller to rotate and generate an attraction to the impeller;
   the perfusion cylinder is configured to inject a perfusate into the interventional tube and enable the perfusate injected from the perfusion cylinder to provide a thrust to the impeller assembly, whereby the impeller is suspendedly rotatable in the interventional tube under a combined action of the thrust and the attraction;
   the motor assembly has a limiting groove, the limiting groove is in communication with the interventional tube, and the perfusate from the perfusion cylinder is adapted to be injected into the limiting groove and then into the interventional tube via the limiting groove;
   the impeller assembly further comprises a transmission shaft; the transmission shaft has a first end being in fixed connection with the impeller, and a second end being opposite to the first end and protruding into the limiting groove; the transmission shaft is configured to rotate along with the impeller; and the second end of the transmission shaft is adapted to be suspended within the limiting groove under the combined action of the attraction of the motor assembly to the impeller and the thrust of the perfusate; and
   the impeller comprises: a hub and a magnetic member arranged in the hub; a first installation groove and a second installation groove are formed in the hub, and the second installation groove is circular and surrounds the first installation groove; and the first end of the transmission shaft is accommodated in the first installation groove, and the magnetic member is accommodated in the second installation groove.

2. The interventional ventricular assist device according to claim 1, wherein
   the motor assembly further comprises a hole assembly; the hole assembly is in communication with the limiting groove, the perfusion cylinder is in communication with the hole assembly, and the perfusate in the perfusion cylinder is enabled to inject into the interventional tube via the hole assembly and the limiting groove sequentially; and
   the hole assembly faces the second end of the transmission shaft, and the perfusate injected into the limiting groove via the hole assembly is adapted to provide a thrust onto the transmission shaft, whereby the transmission shaft and the impeller are suspendedly rotatable under a combined action of the motor assembly and the perfusate.

3. The interventional ventricular assist device according to claim 2, wherein
   the limiting groove comprises: a groove opening, and a bottom wall opposite to the groove opening;
   the groove opening is in communication with the interventional tube; the transmission shaft passes through the groove opening, and the second of the transmission shaft has an end surface in a shape of a convex hemisphere; and
   the hole assembly comprises a first hole and a plurality of second holes; the first hole and the plurality of second holes are all arranged at the bottom wall and are all in communication with the perfusion cylinder and the limiting groove; the first hole is aligned with a center of the end surface of the second end of the transmission shaft; the plurality of second holes are arranged at equal intervals in a circle around the first hole, and the plurality of second holes face the end surface of the second end of the transmission shaft.

4. The interventional ventricular assist device according to claim 3, wherein the bottom wall of the limiting groove is in a shape of a concave hemisphere, and the first hole is arranged at a center of the bottom wall.

5. The interventional ventricular assist device according to claim 2, wherein
   a groove wall of the limiting groove is a cylindrical surface; the hole assembly comprises a first hole and a plurality of second holes; the first hole and the plurality of second holes are all in communication with the perfusion cylinder and the limiting groove; the first hole and the second hole all face the second end of the transmission shaft, the first hole faces an end surface of the second end of the transmission shaft; and the plurality of the second holes are evenly arranged at intervals in a circle around the first hole.

6. The interventional ventricular assist device according to claim 2, wherein the hole assembly comprises a plurality of first holes, and the plurality of first holes all face an end surface of the second end of the transmission shaft, and the plurality of first holes are arranged at intervals around a rotation axis of the transmission shaft.

7. The interventional ventricular assist device according to claim 2, wherein
the motor assembly comprises: a motor casing, and a stator installed and sealed within the motor casing;
the motor casing is in sealed connection with both the interventional tube and the perfusion cylinder;
a first end of the motor casing is arranged at an end of the interventional tube where the liquid outlet is arranged, and the perfusion cylinder is arranged at a second end of the motor casing opposite to the first end of the motor casing; and
both the limiting groove and the hole assembly are defined in the motor casing.

8. The interventional ventricular assist device according to claim 7, wherein the stator and the impeller are arranged along a rotation axis of the impeller.

9. The interventional ventricular assist device according to claim 7, wherein the motor casing defines therein an annular groove, the annular groove is arranged around the limiting groove and is spaced apart from the limiting groove, and the stator is accommodated in the annular groove.

10. The interventional ventricular assist device according to claim 9, wherein
a cylinder extends along a central axis of the annular groove, and both the limiting groove and the hole assembly are formed in the cylinder; and
the cylinder and the annular groove are arranged concentrically; an end of the cylinder protrudes outside of the annular groove, and the end of the cylinder protruding from the annular groove is received in the perfusion cylinder.

11. The interventional ventricular assist device according to claim 7, wherein an outer wall of the motor casing is flush with an outer wall of the interventional tube at a junction of the motor casing and the interventional tube, and the outer wall of the motor casing is flush with an outer wall of the perfusion cylinder at a junction of the motor casing and the perfusion cylinder.

12. The interventional ventricular assist device according to claim 2, wherein
the interventional tube defines therein a first channel, the first channel is in communication with the liquid inlet and the liquid outlet, respectively, and the impeller is accommodated in the first channel; and
the perfusion cylinder defines therein a second channel, and the perfusate injected from the perfusion cylinder is adapted to be injected to the first channel via the second channel, the hole assembly, and the limiting groove sequentially.

13. The interventional ventricular assist device according to claim 1, wherein the impeller comprises a flow guiding hole defined in the impeller; the flow guiding hole has two openings; and a first opening of the flow guiding hole faces the liquid outlet, and a second opening of the flow guiding hole faces the limiting groove.

14. The interventional ventricular assist device according to claim 13, wherein the flow guide hole is one of a plurality of flow guiding holes defined in the impeller, the plurality of flow guiding holes are arranged at equal intervals around the rotation axis of the impeller; and each of the plurality of flow guiding holes has a first opening facing one of liquid outlets, and a second opening facing the limiting groove.

15. The interventional ventricular assist device according to claim 13, wherein the impeller defines therein a first installation groove; the first installation groove comprises: a straight hole portion, and an inclined hole portion in communication with the straight hole portion; an aperture of the inclined hole portion gradually reduces in a direction towards the straight hole portion; the inclined hole portion faces the limiting groove, and the first opening of the flow guiding hole is arranged at a sidewall of the inclined hole portion; and the first end of the transmission shaft is accommodated in the inclined hole portion and the straight hole portion, and is in fixed connection with a sidewall of the straight hole portion.

16. The interventional ventricular assist device according to claim 1, wherein the transmission shaft is arranged at a rotation axis of the impeller, and an extension direction of the transmission shaft is consistent with the rotation axis of the impeller.

17. The interventional ventricular assist device according to claim 1, wherein
the motor assembly is in connection between the interventional tube and the perfusion cylinder;
the impeller comprises: a cylindrical segment, a conical segment, and blades;
the cylindrical segment and the conical segment are integrally connected along an axial direction of the impeller; one end of the cylindrical segment is arranged approximate the motor casing, the conical segment is arranged at another end of the cylindrical segment opposite to the end of the cylindrical segment approaching the motor casing, and the magnetic member is installed within the cylindrical segment; and
each of the blades is spirally distributed on an outer wall of the conical segment.

18. The interventional ventricular assist device according to claim 1, wherein
the interventional tube comprises: a straight tubular segment, and a bend tubular segment having a first end bent and extended from a first end of the straight tubular segment;
a second end of the straight tubular segment which is opposite to the first end is in fixed connection with the motor assembly;
the liquid inlet is arranged at an end of the bend tubular segment opposite to the first end of the bend tubular segment, and the liquid outlet is arranged at a wall of the second end of the straight tubular segment; and
the impeller is rotatably accommodated in the straight tubular segment.

\* \* \* \* \*